(12) United States Patent
Fleischman

(10) Patent No.: US 12,383,228 B2
(45) Date of Patent: Aug. 12, 2025

(54) HIGH RESOLUTION INTRAVASCULAR ULTRASOUND (H-IVUS)

(71) Applicant: THE CLEVELAND CLINIC FOUNDATION, Cleveland, OH (US)

(72) Inventor: Aaron Fleischman, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 602 days.

(21) Appl. No.: 17/715,556

(22) Filed: Apr. 7, 2022

(65) Prior Publication Data

US 2022/0330913 A1    Oct. 20, 2022

Related U.S. Application Data

(60) Provisional application No. 63/176,388, filed on Apr. 19, 2021.

(51) Int. Cl.
*A61B 8/00* (2006.01)
*B06B 1/06* (2006.01)
*H04R 31/00* (2006.01)

(52) U.S. Cl.
CPC .......... *A61B 8/4483* (2013.01); *B06B 1/0688* (2013.01); *H04R 31/00* (2013.01)

(58) Field of Classification Search
CPC ... A61B 8/4483; B06B 1/0688; B06B 1/0207; B06B 1/0215; B06B 2201/76;

(Continued)

(56) References Cited

U.S. PATENT DOCUMENTS 5,635,784 A * 6/1997 Seale .................. F16C 32/0493
310/40 MM
6,641,540 B2 * 11/2003 Fleischman .......... B06B 1/0651
600/459

(Continued)

OTHER PUBLICATIONS

Janjic et.al., A 2-D Ultrasound Transducer With Front-End ASIC and Low Cable Count for 3-D Forward-Looking Intravascular Imaging: Performance and Characterization, IEEE Transactions on Ultrasonics, Ferroelectrics, and Frequency Control, vol. 65, Issue 10, Oct. 2018. (Year: 2018).*

(Continued)

*Primary Examiner* — Jeffrey T Carley
*Assistant Examiner* — Jose K Abraham
(74) *Attorney, Agent, or Firm* — Tarolli, Sundheim, Covell & Tummino LLP

(57) ABSTRACT

High-resolution intravascular ultrasound (H-IVUS) operates under a large acoustic bandwidth, provides high resolution while maintaining good depth penetration, and exhibits other favorable characteristics like focused imaging. A H-IVUS transducer assembly can be manufactured at a low cost using conventional methods commonly utilized in the microelectronics industry. The H-IVUS transducer assembly can include a printed circuit having one or more electrical signal conditioners. One or more convertors made of a polymer and configured to convert electrical energy to acoustic energy and acoustic energy to electrical energy can be formed in place away from the printed circuit. After construction, the one or more formed in place convertors are interfaced to the printed circuit with at least a conductive material.

6 Claims, 15 Drawing Sheets

(58) Field of Classification Search
CPC . B06B 1/0622; B06B 1/0644; B06B 2201/56; H04R 31/00; H10N 30/084; H10N 30/857
See application file for complete search history.

(56) References Cited

U.S. PATENT DOCUMENTS

| | | | | |
|---|---|---|---|---|
| 7,927,275 | B2* | 4/2011 | Kuban | G06T 7/0012 |
| | | | | 600/437 |
| 8,864,674 | B2* | 10/2014 | Corl | B06B 1/0215 |
| | | | | 600/462 |
| 9,259,206 | B2* | 2/2016 | Degertekin | B06B 1/0292 |
| 9,408,588 | B2* | 8/2016 | Huang | B06B 1/0292 |
| 9,700,280 | B2* | 7/2017 | Courtney | G10K 11/352 |
| 2002/0077551 | A1* | 6/2002 | Fleischman | B06B 1/0688 |
| | | | | 600/459 |
| 2004/0039286 | A1* | 2/2004 | Kuban | A61B 8/543 |
| | | | | 600/467 |
| 2004/0054289 | A1* | 3/2004 | Eberle | A61B 8/12 |
| | | | | 600/459 |
| 2005/0197574 | A1* | 9/2005 | Eberle | B06B 1/0622 |
| | | | | 600/437 |
| 2011/0021924 | A1* | 1/2011 | Sethuraman | A61B 5/02007 |
| | | | | 600/463 |
| 2011/0034809 | A1* | 2/2011 | Eberle | B06B 1/0633 |
| | | | | 600/467 |
| 2012/0206014 | A1* | 8/2012 | Bibl | G10K 11/32 |
| | | | | 310/330 |
| 2014/0257107 | A1* | 9/2014 | Rice | A61B 8/12 |
| | | | | 600/459 |
| 2016/0008067 | A1* | 1/2016 | Hadjicostis | A61B 8/445 |
| | | | | 600/439 |
| 2016/0058414 | A1* | 3/2016 | Corl | A61B 8/4444 |
| | | | | 600/463 |
| 2018/0035891 | A1 | 2/2018 | Van Soest et al. | |
| 2020/0037985 | A1* | 2/2020 | Stigall | A61B 8/445 |
| 2021/0113195 | A1* | 4/2021 | van Rens | B06B 1/0292 |

OTHER PUBLICATIONS

Chen et.al., A Single-Cable PVDF Transducer Readout IC for Intravascular Photoacoustic Imaging, 2015 IEEE International Ultrasonics Symposium Proceedings, 2015 (Year: 2015).*
Chen, Chao, et al. "A single-cable PVDF transducer readout IC for intravascular photoacoustic imaging." 2015 IEEE International Ultrasonics Symposium (IUS). IEEE, 2015.
Fleischman, Aaron, et al. "Miniature high frequency focused ultrasonic transducers for minimally invasive imaging procedures." Sensors and Actuators A: Physical 103.1-2 (2003): 76-82.
Lockwood, G. R., and C. R. Hazzard. "Development of small aperture polymer transducers for high frequency imaging." 1997 IEEE Ultrasonics Symposium Proceedings. An International Symposium (Cat. No. 97CH36118). vol. 2. IEEE, 1997.
Ketterling, Jeffrey A., et al. "Design and fabrication of a 40-MHz annular array transducer." IEEE transactions on ultrasonics, ferroelectrics, and frequency control 52.4 (2005): 672-681.

* cited by examiner

50 ─▸

```
┌─────────────────────────────────────────────────────────────┐
│ FORM ONE OR MORE ELECTRICAL SIGNAL CONDITIONERS ON A PRINTED│
│                           CIRCUIT                           │
│ 52                                                          │
└─────────────────────────────────────────────────────────────┘
                              │
                              ▼
┌─────────────────────────────────────────────────────────────┐
│              FORM ONE OR MORE CONVERTORS IN PLACE           │
│ 54                                                          │
└─────────────────────────────────────────────────────────────┘
                              │
                              ▼
┌─────────────────────────────────────────────────────────────┐
│  INTERFACE THE ONE OR MORE FORMED IN PLACE CONVERTORS TO THE│
│                       PRINTED CIRCUIT                       │
│ 56                                                          │
└─────────────────────────────────────────────────────────────┘
```

```
┌─────────────────────────────────────────────────────────────┐
│  TRANSFER CONVERTOR MATERIAL TO A PRECISE LOCATION ON A     │
│      PRINTED CIRCUIT USING A SHAPED END EFFECTOR            │
│ 62                                                          │
└─────────────────────────────────────────────────────────────┘
                              │
                              ▼
┌─────────────────────────────────────────────────────────────┐
│  APPLY ONE OR MORE OF PRESSURE, HEAT, AND VIBRATION TO THE  │
│     CONVERTOR MATERIAL USING THE SHAPED END EFFECTOR        │
│ 64                                                          │
└─────────────────────────────────────────────────────────────┘
                              │
                              ▼
┌─────────────────────────────────────────────────────────────┐
│  INTERFACE THE SHAPED CONVERTOR MATERIAL TO THE PRINTED     │
│       CIRCUIT VIA A CONNECTION MECHANISM                    │
│ 66                                                          │
└─────────────────────────────────────────────────────────────┘
```

FIG. 6

HIGH RESOLUTION INTRAVASCULAR ULTRASOUND (H-IVUS)

CROSS-REFERENCE TO RELATED APPLICATIONS

This application claims the benefit of U.S. Provisional Application Ser. No. 63/176,388, filed 19 Apr. 2021, entitled "HIGH RESOLUTION INTRAVASCULAR ULTRASOUND", the entirety of which is incorporated by reference for all purposes.

GOVERNMENT SUPPORT

This invention was made with government support under HL119810 awarded by the National Institutes of Health. The government has certain rights in this invention.

TECHNICAL FIELD

The present disclosure relates generally to intravascular ultrasound (IVUS) and, more specifically, to a transducer assembly that enables high resolution IVUS (H-IVUS) imaging and methods for constructing the H-IVUS transducer assembly.

BACKGROUND

Intravascular ultrasound (IVUS) imaging is a technique for imaging central and peripheral blood vessels using sound waves, not ionizing radiation. IVUS can provide images with good depth penetration for identification and classification of stent deployment, identification of stent tissue coverage, identification of Thin-Cap Fibroatheromas (TCFAs), assessment of plaque erosion, assessment of soft plaque burden, real-time classification of plaques for treatment planning, and more. However, IVUS generally has poor resolution that is significantly worse than other techniques such as intravascular optical coherence tomography (IVOCT). One solution to improve resolution is combined IVOCT-IVUS, but such a combined approach has limitations in terms of cost, complexity, and technical constraints.

SUMMARY

High-resolution intravascular ultrasound (H-IVUS) can provide focused imaging with a high (near optical coherence tomography (OCT)-level) resolution that maintains the good depth penetration characteristic of traditional IVUS and provides other favorable characteristics at a low cost (less expensive than current IVUS catheters), while being manufactured using conventional methods commonly utilized in the microelectronics industry. Notably, H-IVUS does not require the use of intravascular OCT to reach this favorable spatial resolution.

In an aspect, the present disclosure includes a transducer assembly that can be used for H-IVUS. The transducer assembly can include a printed circuit having one or more electrical signal conditioners; and one or more formed in place convertors made of a polymer and configured to convert electrical energy to acoustic energy and acoustic energy to electrical energy. The one or more formed in place convertors are interfaced to the printed circuit with at least a conductive material.

In another aspect, the present disclosure includes a method for constructing the transducer assembly that can be used for H-IVUS. The method includes transferring convertor material to a precise location on a printed circuit using a shaped end effector; applying one or more of pressure, heat, and vibration to the convertor material using the shaped end effector to irreversibly deform the convertor material to match a shape of the shaped end effector; and interfacing the deformed convertor material to the printed circuit via a connection mechanism. The connection mechanism includes at least a conductive material.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 5-7 are process flow diagrams of methods for assembling a H-IVUS transducer;

DETAILED DESCRIPTION

I. Definitions

Figure 1:
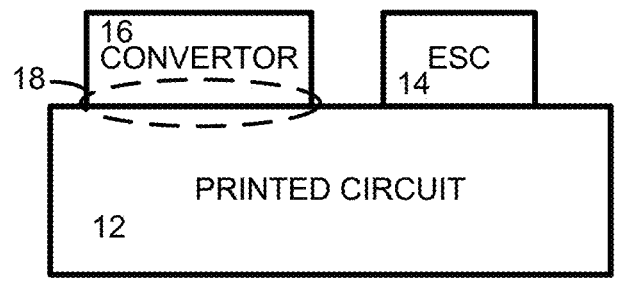
FIG. 1 is an illustration of a fabricated high-resolution intravascular ultrasound (H-IVUS) transducer assembly.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "intra vascular ultrasound (IVUS)" refers to a medical imaging methodology specifically using a specially designed catheter with a miniaturized ultrasound transducer attached to the distal end of the catheter. High-resolution IVUS (H-IVUS) refers to an IVUS system configured for high spatial resolution and other favorable advantages.

As used herein, the term "spatial resolution" includes both axial resolution and lateral resolution.

As used herein, the term "axial resolution" refers to the depth of penetration of sound waves. Generally, IVUS and H-IVUS exhibit good axial resolution. Axial resolution (Rax) can be expressed as $$R_{ax} = \frac{1}{2}\frac{c}{BW},$$

where BW is bandwidth.

As used herein, the term "lateral resolution" refers to the width across a section of anatomy. The term "resolution" can be used interchangeably with "lateral resolution". Generally, IVUS exhibits a lateral resolution/resolution that is significantly worse than other techniques such as intravascular optical coherence tomography (IVOCT), but H-IVUS has a lateral resolution that is the same or better than other techniques. Lateral resolution (Rlat) can be expressed as $$R_{lat} = \bar{\lambda}\left(\frac{\text{focal length}}{\text{diameter}}\right) = \bar{\lambda} \times (f\text{-number}).$$

As used herein, the term "transducer" refers to a device that can send and receive energy and convert this energy to another form (e.g., an ultrasound transducer converts electrical energy to acoustic energy and acoustic energy to electrical energy) and may have to send information along a distance. For example, an H-IVUS ultrasound transducer can include a convertor that facilitates the energy conversion and an electrical signal conditioner (ESC), which may include an amplifier.

As used herein, the term "printed circuit board (PCB)" refers to at least one layer of nonconductive substrate that mechanically supports and electronically connects electrical or electronic components using conductive tracks, pads, and other features etched from a layer fixed to the nonconductive substrate.

As used herein, the term "electrical signal conditioner (ESC)" relates to a device that can manipulate a signal to meet requirements necessary for further processing. In one example, an electrical signal conditioner can include an amplifier.

As used herein, the term "application specific integrated circuit (ASIC)" refers to an integrated circuit (IC) chip customized for a particular use, rather than intended for a general-purpose use.

As used herein, the term "convertor" refers to a device that converts one from of energy to another form of energy. The convertor can be formed in place and later interfaced with a PCB.

As used herein, the term "piezo" refers to a material that exhibits piezoelectricity (an electric charge that accumulates in certain solid materials in response to applied mechanical stress). One type of material that exhibits piezoelectricity is a piezopolymer.

As used herein, the term "patient" refers to any warm-blooded organism (e.g., a human being, a primate, a cat, a dog, a rabbit, a mouse, etc.).

II. Overview

Intravascular ultrasound (IVUS) can be used to provide images of central and peripheral blood vessels that have a good depth penetration, but poor resolution. High-resolution intravascular ultrasound (H-IVUS) expands the acoustic bandwidth of traditional IVUS, provides high resolution (at near optical coherence tomography (OCT) levels), and maintains the good depth penetration characteristic of traditional IVUS. H-IVUS also provides other favorable characteristics like focused imaging and a low cost of manufacturing by using conventional methods commonly utilized in the microelectronics industry. Specific technological improvements include: (1) manufacture of focused piezopolymer transducers to improve lateral resolution; (2) widebandwidth transducers to enable improved axial resolution (e.g., of ~18 μm); (3) a flexible broadband transducer design to enable imaging over a wide frequency range (e.g., from 20 MHz to 80 MHz) using different excitation pulse frequencies and pulse inversion to obtain harmonic data; (4) focusing transducers to produce peak harmonic responses within the target vessel unlike unfocussed transducers, which produce peak harmonic responses at the Raleigh length, beyond the target vessel; (5) H-IVUS transducers and electronics can be assembled using standard printed circuit board (PCB) assembly methods to create H-IVUS PCBs and can be tested prior to catheter assembly to greatly decrease manufacturing costs compared to standard IVUS, which is typically tested only after the catheter is built; and (6) broadband fundamental and harmonic bands can be obtained with pulse inversion, providing additional scattering information from tissues that enables machine learning plaque classification.

H-IVUS can be used in the diagnosis and treatment of coronary artery disease and peripheral artery disease, assessment of stent placement, forward looking needle guidance, high resolution tissue imaging for minimally invasive surgery, and the like. H-IVUS can meet needs of clinicians and clinical researchers; several examples of the way H-IVUS can meet these needs include: characterization of stent deployment; identification of stent tissue coverage; identification of TCFAs; assessment of plaque erosion; assessment of soft plaque burden; full pullback, real time classification of plaques for treatment planning; and more. Additionally, H-IVUS is superior to combined IVOCT-IVUS, which is limited in terms of cost, complexity, and technical constraints. For example, in simultaneous IVOCT-IVUS acquisitions, one must accommodate IVUS, the slower imaging modality, limiting pullback length or requiring a longer duration contrast agent flush to clear blood, both options being clinically undesirable.

III. Systems

An aspect of the present disclosure can include a system that includes a high-resolution intravascular ultrasound (H-IVUS) transducer assembly 10 (shown in FIG. 1) that enables H-IVUS imaging. The system can also include a catheter (e.g., of a size traditionally used for IVUS) that the H-IVUS transducer assembly 10 can reside on or within. For example, the H-IVUS transducer assembly 10 can be mounted at or near an open portion of the catheter (see, e.g., FIG. 15) to provide a superior spatial resolution to traditional IVUS systems while being significantly less expensive. A catheter with a H-IVUS transducer assembly 10 can be used in the diagnosis and treatment of coronary artery disease and peripheral artery disease, assessment of stent placement, forward looking needle guidance, high resolution tissue imaging for minimally invasive surgery, and the like. It should be noted that the elements of the figures are not drawn to scale. For example, the convertor material may be thinner than is illustrated in the figures.

In a H-IVUS transducer assembly 10, a convertor 16 (e.g., especially when made of a Piezo polymer) provides a generally weak signal and requires an electrical signal conditioner (ESC) 14 that includes at least an amplifier so that the signal can be transmitted across a distance. The amplifier must interface with the convertor 16 to enable strong signal transmission down the length of the catheter. Accordingly, the convertor 16 and the ESC 14 including the amplifier can be co-located on a printed circuit 12. Notably, a Piezo polymer material generally has a high output impedance, which results in signal attenuation when coupled into a 50 ohm coaxial cable. While Piezo polymers have lower piezo response than ceramics (like lead zirconate titanate (PZT)), the dominant signal degradation is this mismatch. Further, even small area ceramic materials suffer from this effect as the output impedance is inversely proportional to the area of the transducer. This issue is exacerbated for Piezo polymer transducer as they have a significantly lower dielectric constants than ceramics.

An example of the H-IVUS transducer assembly 10 is shown in FIG. 1. The H-IVUS transducer assembly can be formed on a printed circuit board (PCB) having a printed circuit 12 thereon or therein. The printed circuit 12 can have one or more ESCs 14 thereon. Although only a single ESC 14 is shown in FIG. 1, this is only for ease of illustration and explanation. It will be understood that any number of ESCs can exist on the printed circuit 12 based on requirements of the intended application/use. In one example, the ESC 14 can be embodied on or in one or more application specific integrated circuits (ASICs) that is formed on/mounted to the printed circuit 12.

One or more ESC 14 can interface with one or more convertors 16 on the printed circuit 12 (for example, the ESC 14 can be configured to interface with one or more convertors 16). The interface between the ESC 14 and the one or more convertors 16 can be an electrical and/or mechanical coupling. Although only a single convertor 16 is shown in FIG. 1, this is only for ease of illustration and explanation. It will be understood that any number of convertors can exist on the printed circuit 12 based on requirements of the intended application/use.

The convertor 16 can be configured to convert electrical energy to acoustic energy and acoustic energy to electrical energy. The convertor 16 can include one or more piezoelectric materials. At least one of the one or more piezoelectric materials can be a polymer (e.g., a piezoelectric polymer). The piezoelectric polymer (also referred to as a "Piezo polymer") can be a thermoplastic, which may include polyvinylidene difluoride (PVDF) and/or trifluoroethylene (TrFE). For example, the piezoelectric polymer may be PVDF or PVDF-TrFE. The convertor 16 can have a shape that can facilitate at least a portion of the conversion of electrical energy to acoustic energy and acoustic energy to electrical energy. The shape of the convertor 16 (e.g., shape of an emitter of the convertor 16) can be designed to compensate for aberration of the ultrasound beam by the catheter. Example shapes include generally parabolic, generally concave, or any arbitrary shape. When the shape is generally concave or parabolic, it should be understood that the shapes of each convertor 16, if there are multiple convertors 16, can be different (e.g., between different convertors 16 on the same printed circuit 12 or between different printed circuits 12) enabling different depths of energy focus.

The convertor 16 can be interfaced to the printed circuit 12 with at least a conductive material (at interface 18). In some instances, the conductive material can be ductile. As an example, the conductive material can be a curable conductive fluid. As another example, the interface 18 can be created by a non-conductive epoxy and the conductive material can be already within the printed circuit 12.

The H-IVUS transducer assembly 10 can be manufactured using conventional methods commonly utilized in the microelectronics industry. The H-IVUS transducer assembly 10 can include the printed circuit 12 on a PCB, at least one ESC 14 formed on the printed circuit 12, and one or more convertors 16 that can interface to be printed circuit at interface 18. In one example, the convertor 16 can be made inside of or from a PCB. In another example, the H-IVUS transducer assembly 10 can include a PCB hybrid where at least the convertor 16 is manufactured separately from the PCB and then placed onto a PCB; in this case, the convertor 16 can be constructed on one or more external substrates where it is then singulated and mated to a PCB using pick and place technology. The convertor 16 can be shaped either via application of a uniform pressure or by using a mandrel (either before or after being mated to the PCB). In the example where the convertor 16 is a Piezo polymer film, this approach to shaping maximizes the number of transducers per unit area of the Piezo polymer film.

Figure 2:
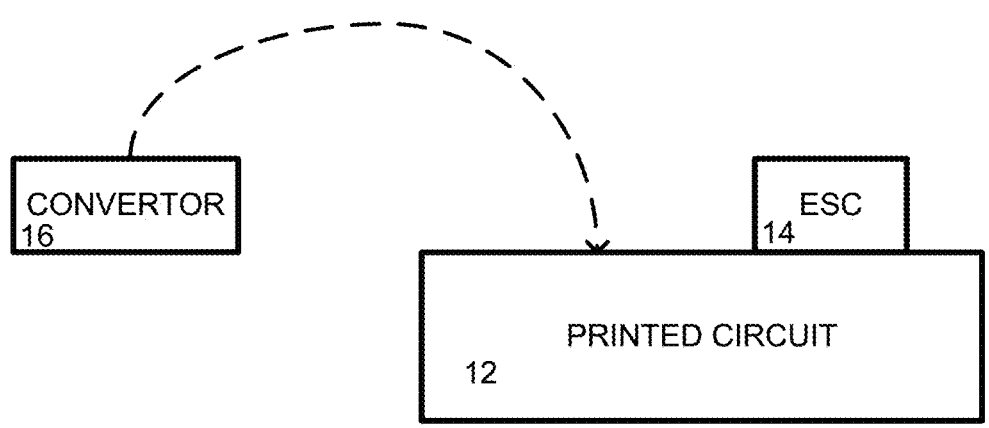
FIGS. 2 and 3 are illustrations of different ways the H-IVUS transducer assembly of FIG. 1 can be fabricated.

FIG. 2 shows an example 20 where the ESC 14 is formed on the printed circuit 12 (or PCB), while the convertor 16 is formed in a separate place. The convertor 16 in this example can be referred to as a "formed in place" convertor 16. It should be noted that the convertor 16 can be shaped either before or after it mates/interfaces with the printed circuit 12 or PCB. In some instances, the printed circuit 12 or PCB can include a pre-shaped receiving area for the convertor 16 that is configured to accept the convertor 16. In other instances, the printed circuit 12 or PCB can include and/or be formed of a material that is permanently deformable under pressure and/or heat (e.g., pressure and/or heat that is due to placement of the formed in place convertor 16). The material can also have at least one acoustic property, which can be complementary to the acoustic properties provided by the material of the convertor 16 (e.g., the Piezo polymer).

Although the convertor 16 can be formed on/in the PCB, it is often preferable to form the convertor 16 independently from the PCB. The rationale for forming the convertor 16 separately from the PCB is as follows: (1) custom electronics in the form of an Application Specific Integrated Circuit (ASIC or computer chips) can be readily designed and fabricated at low costs; (2) chip on board technology where the ASIC is directly attached to the PCB by a process called flip chip bonding is a high yield standard electronics fabrication process; (3) high performance ASICs and PCBs with suitable form factors for placement within a 3 F catheter have been demonstrated; (4) methods for forming shaped piezo polymer transducers in PCBs compatible with flip chip bonding have been demonstrated creating a hybrid PCB transducer package; (5) these hybrids can be attached to fine wire cables using standard electronic fabrication methods; (6) the hybrid PCB transducer package can be functionally tested before making an IVUS catheter demonstrating significant cost avoidance in comparison to building catheters with only functioning transducers.

Figure 3:
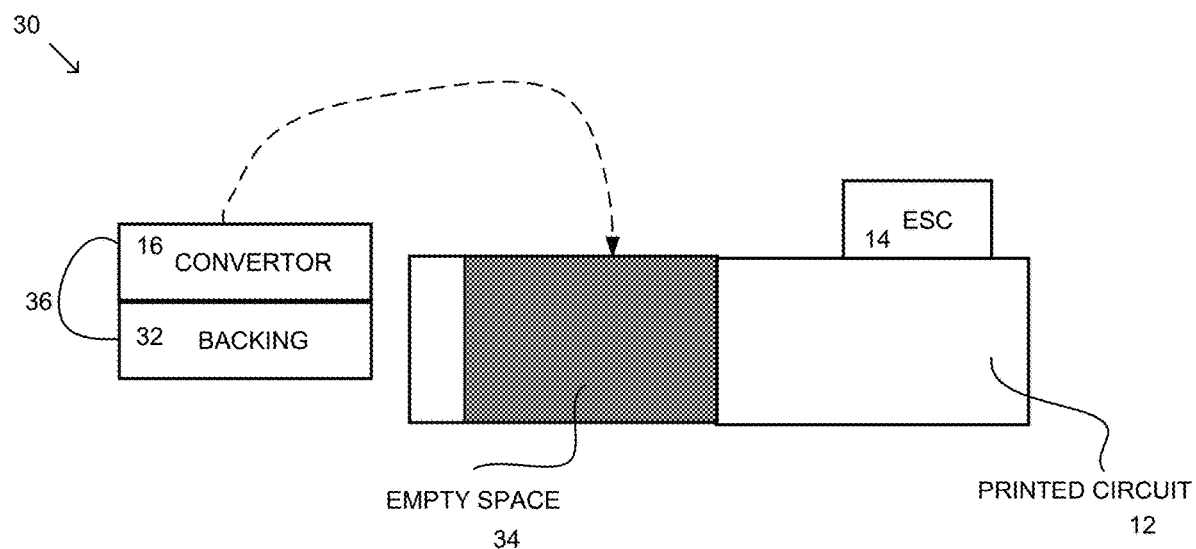

FIG. 3 shows a way for the convertor 16, formed outside the PCB, to be placed within the PCB. The convertor 16 can be mated with a backing 32 (e.g., a material that is non-conductive and/or conductive with appropriate acoustic properties for the transducer) to become a focused transistor 36. In some instances, the backing 32 material can include an epoxy material. In other instances, a bottom electrode patterned on the polymer film or on top of the backing material before applying the polymer film and adhering it with conductive spray.

Figure 4:
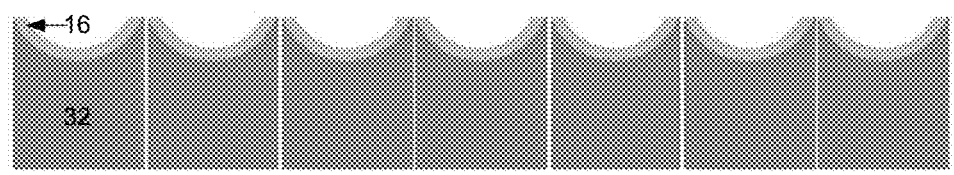
FIG. 4 is an illustration of a cross-section of a multiplicity of focused H-IVUS transducers.

The focused transistor 36 can be placed within an empty space 34 within a printed circuit 12 (e.g., using pick and place technology). In the example shown in FIG. 3, the ESC 14 can be formed on the PCB 12. Air pressure can be used to shape the convertor 16 either before placing in the PCB 12 or after placement in the PCB. An example of a multiplicity (e.g., 2 or more) of shaped focused transistors is shown in FIG. 4. Each of the multiplicity of shaped focused transistors can have a convertor 16 mated with a backing 32.

IV. Methods

Another aspect of the present disclosure can include methods 50-70 (FIGS. 5-7) for assembling a high-resolution intravascular ultrasound (H-IVUS) transducer (like the H-IVUS transducer shown in FIGS. 1-4). The methods are illustrated as process flow diagrams with flowchart illustrations. For purposes of simplicity, the methods are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50-70.

As noted above, the H-IVUS transducer assembly (e.g., element 10 of FIG. 1) can be manufactured using conventional methods commonly utilized in the microelectronics industry. The H-IVUS transducer assembly can include the printed circuit on a PCB, at least one ESC formed on the printed circuit, and one or more convertors that can interface to the printed circuit at an interface. In one example, the convertor can be made inside of or from a PCB. In another example, the H-IVUS transducer assembly can include a PCB hybrid where at least the convertor is manufactured separately from the PCB and then placed onto a PCB; in this case, the convertor can be constructed on one or more external substrates where it is then singulated and mated to a PCB using pick and place technology. The convertor can be shaped either via application of a uniform pressure (e.g., by applying air) or by using a mandrel (either before or after being mated to the PCB). In the example where the convertor 16 is a Piezo polymer film, this approach to shaping maximizes the number of transducers per unit area of the Piezo polymer film.

The material of the convertor (e.g., a Piezo polymer) is easy to shape to improve lateral resolution, which enables superior axial resolution and optimized signal excitation. The convertor requires at least an amplifier in conjunction therewith in order to enable strong signal transmission down a length of catheter (in an IVUS catheter application). Thus, the convertor and the electronics must be co-located. Using pick and place technology, the transducer can be mated to a PCB to co-locate the transducer and the electronics.

FIG. 5 illustrates a method 40 for assembling a H-IVUS transducer assembly. At Step 52 one or more electrical signal conditioners (ESC 14) can be formed on a printed circuit (or PCB) (printed circuit 12). At Step 54, one or more convertors (e.g., Piezo polymer transducers) (convertor 16) can be formed in place (away from the printed circuit). At Step 56, the one or more formed in place convertors can be interfaced to the printed circuit (at interface 18).

FIG. 6 illustrates another method 50 for assembling a H-IVUS transducer assembly. At Step 62, a convertor material can be transferred to a precise location on a printed circuit (or PCB) using a shaped end effector (e.g., a mandrel). The shaped end effector can include a contoured shape in two dimensions or three dimensions and, in some instances, can include a non-stick coating, a polished surface, a micro-patterned surface, or the like. The shaped end effector can include one or more sensors (e.g., one or more of a pressure sensor, a displacement sensor, a rotation sensor, a temperature sensor, or the like). The one or more sensors can provide feedback and control the shaped end effector as the convertor material is irreversibly deformed and may help to reduce friction and/or improve surface finish during the manufacturing/forming process. It should be noted that at least one of the one or more convertors and/or one or more additional components can be applied to one or both sides of the printed circuit. In some instances, the shaped end effector can be attached to an automation machine that controls movement of the shaped end effector along one or more motion axes.

At Step 64, one or more of pressure, heat, and vibration can be applied to the convertor material using the shaped end effector to irreversibly deform the convertor material to match a shape of the shaped end effector. The pressure, heat, and vibration can also irreversibly deform the printed circuit. Alternatively, the printed circuit can be pre-formed with an area (or a deformation) to accept the convertor (e.g., a preshaped receiving area). An electric field can be applied to the formed convertor material. For example, the shaped end effector can be configured to be used as an electrode to generate an electrical field.

At Step 66, the shaped convertor material can be interfaced to the printed circuit via a connection mechanism. The connection mechanism can include a conductive material, like a curable conductive fluid (e.g., a conductive adhesive that is applied to one or both surfaces of the printed circuit and the deformed convertor material). The connection mechanism can also include a non-conductive epoxy and the conductive aspects can be within the printed circuit. It should be noted that a shape of the printed circuit and the convertor when attached compensates for one or more dimensional changes due to shaping recoil, stress relieving, or the like.

Figure 7:
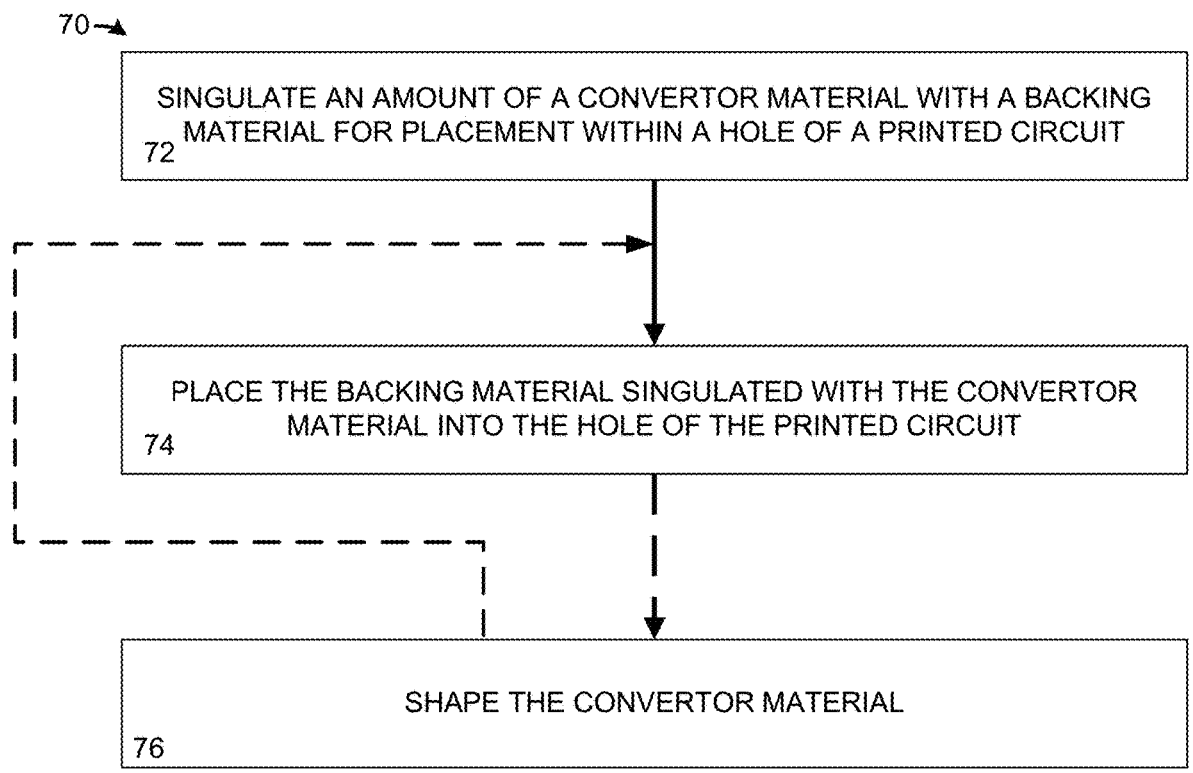

FIG. 7 illustrates another method 70 for making a H-IVUS transducer. In this example, the convertor, which can be a polymer with dielectric properties, can be formed outside the PCB. At 72, an amount of a convertor material can be singulated with a backing material (e.g., focused transistor 36) for placement within a hole (e.g., empty space 34) of a printed circuit. For example, the backing material can include epoxy. At 74, the backing material singulated with the convertor material can be placed into the hole of the printed circuit using a pick and place method. At 76, the convertor material can be shaped, either between steps 72 and 74 or after step 74. The shaping can be done by applying air pressure to the convertor material to shape the convertor material. For example, after shaping, the convertor material comprises a spherically shaped aperture section with a depth into the backing material controlled by the air pressure. This method can work for a plurality of backing materials singulated with the convertor material (focused transducers 36) that are placed in a plurality of holes of printed circuits using the pick and place method; the focused transducers can be shaped using air pressure on a form with circular apertures before mating, after mating, but before placement, or after placement.

V. Experimental

This experiment shows an example high resolution Intravascular Ultrasound (H-IVUS) Transducer, which is manufactured at a low cost using conventional methods commonly utilized in the microelectronics industry and improves spatial resolution of traditional IVUS. The H-IVUS transducer has one or more high-bandwidth piezoelectric micro-machined ultrasound transducers (PMUTs) and one or more front-end interface amplifiers (analog front ends (AFEs)) on a printed circuit. The one or more PMUTs are interfaced with the printed circuit.

Piezoelectric Micro-Machined Ultrasonic Transducer (PMUT)

The H-IVUS transducer has one or more high-bandwidth PMUTs. PMUTs provide superior resolution to image small critical structures while still having high soft tissue penetration for soft plaque evaluation.

PMUTs are generally fabricated from piezoelectric films, such as poly[(vinylidenefluoride-co-trifluoroethylene] (PMUT-TrFE). The thickness of a PMUT-TrFE film was chosen to resonate at 40 MHz (sufficient bandwidth exists to capture the $2^{nd}$ harmonic at 80 MHz and a sub-harmonic at 20 MHz). This wide bandwidth allows echo data collection at the harmonic frequencies for image sharpening.

The transducer was spherically focused using a custom forming tool to define the focal length. The transducer impedance was measured and modeled as a 2.2 pF capacitor with 30 kΩ leakage resistance at 40 MHz. Acoustic modeling estimated the transducer SNR to be 88 dB, however, due to the high impedance, this SNR would be reduced by 19 dB in a 50Ω system.

PMUT-TrFE, compared to conventional ceramic transducers and capacitive micro-machined ultrasonic transducers (CMUT), has higher bandwidth and output impedance. Hence, PMUT-TrFE transducers cannot be directly connected to the conventional, 500 coaxial cable without significant insertion loss.

Analog Front End (AFE) Interface

To buffer the high impedance transducer signal and improve SNR, an Analog Front End (AFE) Application Specific Integrated Circuit (ASIC) was designed to interface with a PMUT-TrFE transducer. The AFE ASIC was developed to withstand high-voltage pulses during imaging, while retaining low noise amplification of acoustic echoes from tissue targets.

Figure 8:
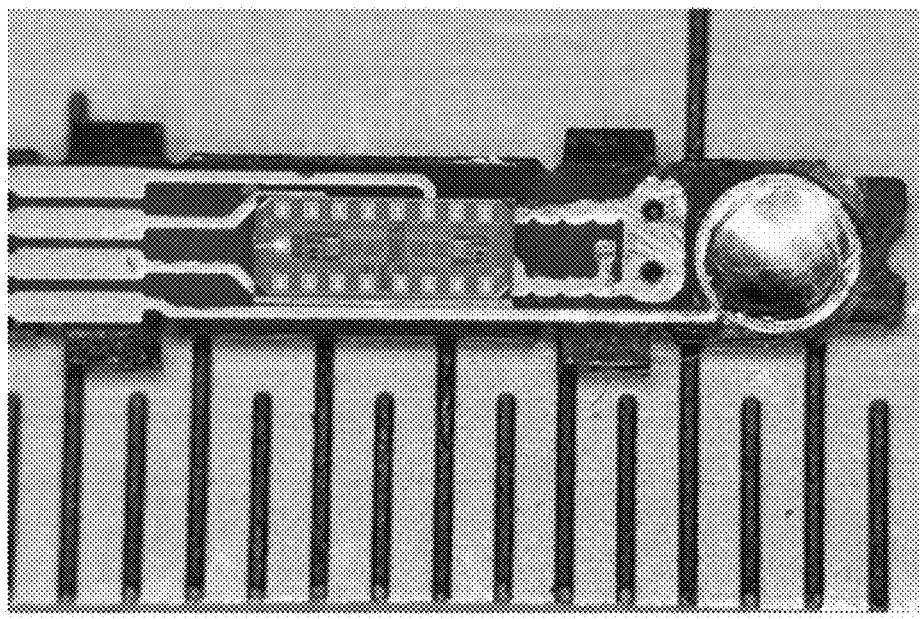
FIG. 8 is an image of a miniaturized printed circuit board (PCB) that was developed for flip-chip bonding of an analog front end (AFE) application specific integrated circuit (ASIC) next to an integrated high bandwidth piezoelectric micro-machined ultrasonic transducer-poly[vinylidenefluoride-co-trifluoroethylene] (PMUT-TrFE) used in the experiment described below.

The ASIC had a width of 0.85 mm allowing for flip-chip bonding. The ASIC was twice as long as needed to include test circuits. Preliminary bench characterization data is presented that the ASIC can interface with the PMUT-TrFE transducer, withstand a 100V pulse, pre-amplify, and buffer the echo signal with appropriate post-high-voltage-pulse recovery time. It is also shown that the fabricated silicon could be integrated with a PMUT-TrFE transducer on a miniaturized PCB that fits within a standard 1 mm catheter (FIG. 8).

The AFE duplexes the high voltage pulses and amplifies and buffers the echo signals. A shunt/series-duplexer topology was considered because modern integrated fabrication processes do not provide high voltage FETs to withstand the pulsing voltage. Instead, an active limiter clamps the input voltage under the allowable voltage level of 7V peak (drain-source breakdown voltage of the process). This topology allowed the ASIC to be fabricated with standard low-voltage processes with high breakdown voltage metal-insulator-metal capacitors.

Figure 9:
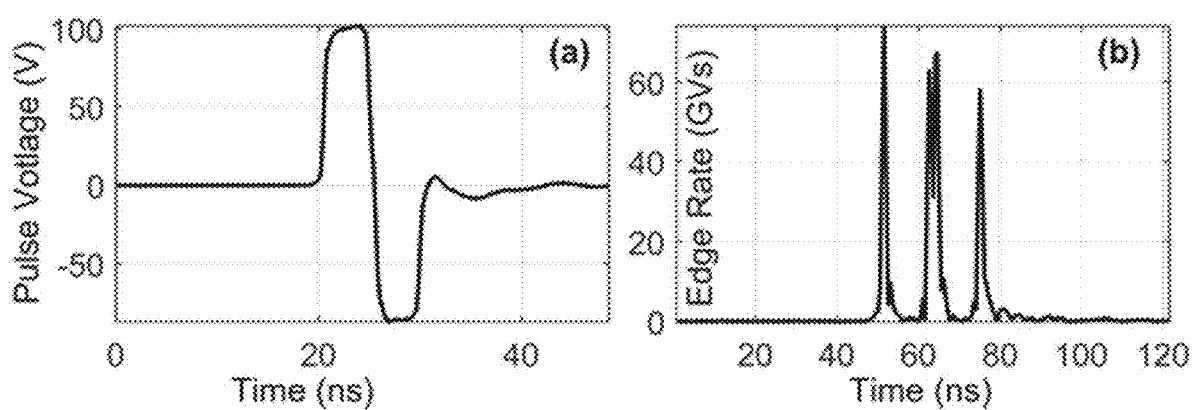
FIG. 9 shows graphs of the pulse voltage and edge rate of the H-IVUS pulser from the experiment described below.

The active limiter was designed based on the current flow into the low voltage part of the circuit, namely the amplifier and buffer. The pulse shape of a commercial IVUS device (Avtech AVB1-3-C, Avtech Electrosystems) was used to model the current surge during transducer excitation. The pulse had a maximum pulsing voltage $V_p$ of 101V and a maximum edge rate of 74 GV/s (FIG. 9). Maximum edge rate determined the maximum current that could flow into the amplifiers and hence the active limiter performance requirement.

Figure 10:
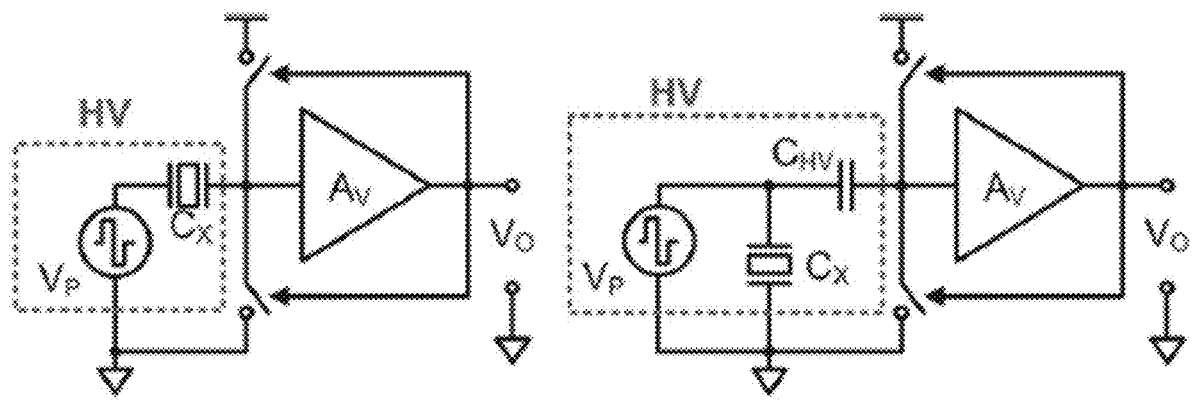
FIG. 10 is a diagram of a shunt duplicator (a) and a series duplicator (b), both using an active limiter from the experiment described below.

In the fabricated design, a series-duplexer topology was chosen over the shunt-duplexer topology (FIG. 10) because shunt duplexers require an IVUS pulser to provide low noise ground during receiving; this is uncommon since the IVUS pulser is normally high impedance for safety reasons. The series duplexer has a significantly lower clamping current, minimizing the size of the limiter parasitic impedance.

High Voltage Coupling Capacitor

The AFE circuit was designed to have two high voltage coupling capacitors $C_{HV}$ in series, an LNA, and an active limiter to implement the series-duplexer topology. The design was optimized for signal chain gain and noise of the series-duplexer circuit. The optimized design variable was the size of the high voltage coupling capacitor $C_{HV}$, which was sized to present enough input impedance to limit current during high voltage pulsing without overly loading the transducer during echo recovery.

A bigger coupling capacitor reduces insertion loss and presents higher signal amplitude at the low noise amplifier $A_V$ input. However, a bigger coupling capacitor also results in higher clamping current during pulsing cycles. This increases the size of limiter transistors, which increases the parasitic capacitance of the amplifier, and reduces signal gain. Therefore, this amplifier topology has a process-dependent optimum $C_{HV}$ based on the transducer capacitance.

Figure 11:
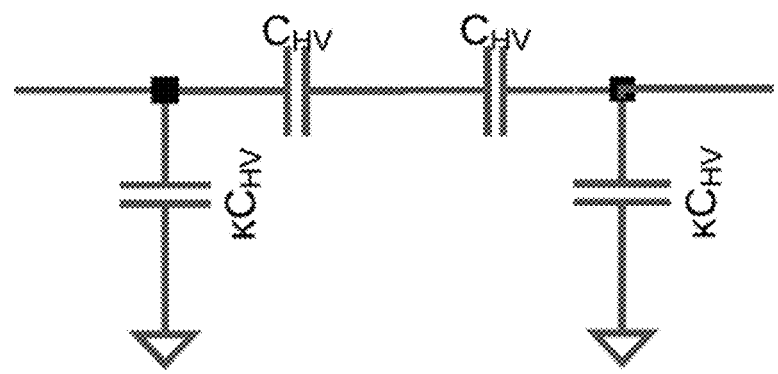
FIG. 11 is a parasitic model of the coupling capacitor from the experiment described below.

The AFE was designed for the OnSemi I3T80 process, which offers metal-insulator-metal (MIM) capacitors rated to 50V. Two high voltage capacitors were put in series to implement the coupling capacitor with 100V pulse voltage tolerance. Because the MIM capacitor had low capacitance per area, it introduced non-negligible substrate-coupled parasitic capacitance (FIG. 11). The ratio of substrate-coupled parasitic capacitance to high voltage capacitor was modeled as $\kappa = C_{HV}/C_{HVpar}$. The process dependent parameter $\kappa$ is an essential parameter in the optimization. For the I3T80 process $\kappa=15\%$.

Active Limiter

The active limiter clamps the voltage below the FET gate breakdown voltage during the pulsing period. The active limiter used two transistors with gates tied to the output of the LNA. During high voltage pulsing, as the input voltage of LNA approaches threshold (hysteretic and set by the output voltage of the LNA), the comparator will turn on either the NMOS or PMOS to source or sink the incoming current.

Active limiter transistors contribute significant input parasitic capacitance to the LNA due to their large size. The minimum size of active limiter transistors was related to coupling capacitor size and maximum edge rate by a process dependent parameter $\gamma$, $$\gamma = C_{LIM}/\frac{1}{2}C_{HV} = \alpha\left(\frac{dV_p}{dt}\right)_{max}$$

where $\alpha$ is the ratio of parasitic capacitance to limiter transistor current capability. $\alpha=9.3$ pF/A and $\gamma=6.9$ were calculated for the I3T80 process using simulations. These values were used for SNR optimization of the amplifier.

The active limiter size also affects the amplifier's post-pulse-recovery time because a large limiter induces more parasitic capacitance that holds more charge after pulsing.

Low Noise Amplifier (LNA) and Buffer

Figure 12:
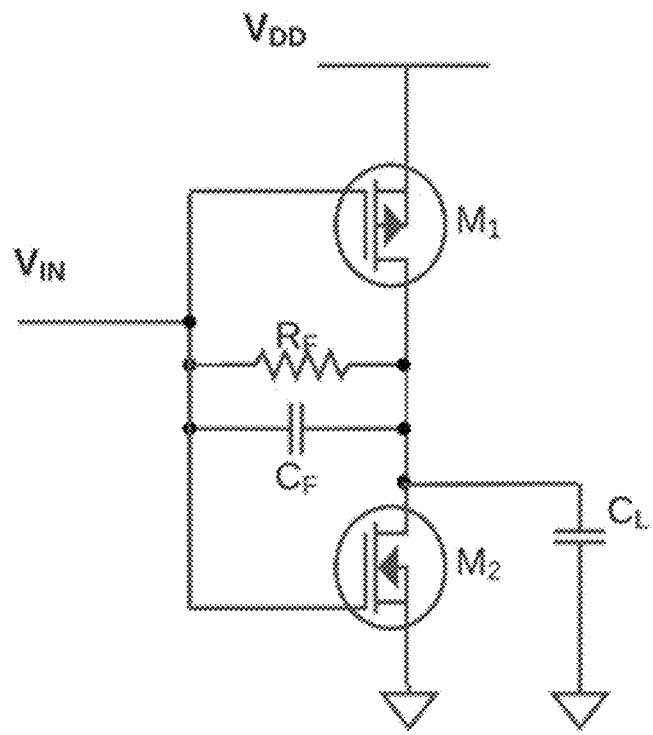
FIG. 12 is a diagram of the low noise amplifier (LNA) implemented using a self-biased push-pull topology with resistive feedback from the experiment described below.

The LNA pre-amplifies and sets the bandwidth of the echo signal. It was implemented using a self-biased push-pull topology with resistive feedback (FIG. 12). Feedback resistance $R_f$ sets the amplifier's gain. The combination of feedback capacitance $C_f$ (the sum of $C_{gd}$ of the two amplifier transistors) and $R_f$, sets the LNA bandwidth.

Figure 13:
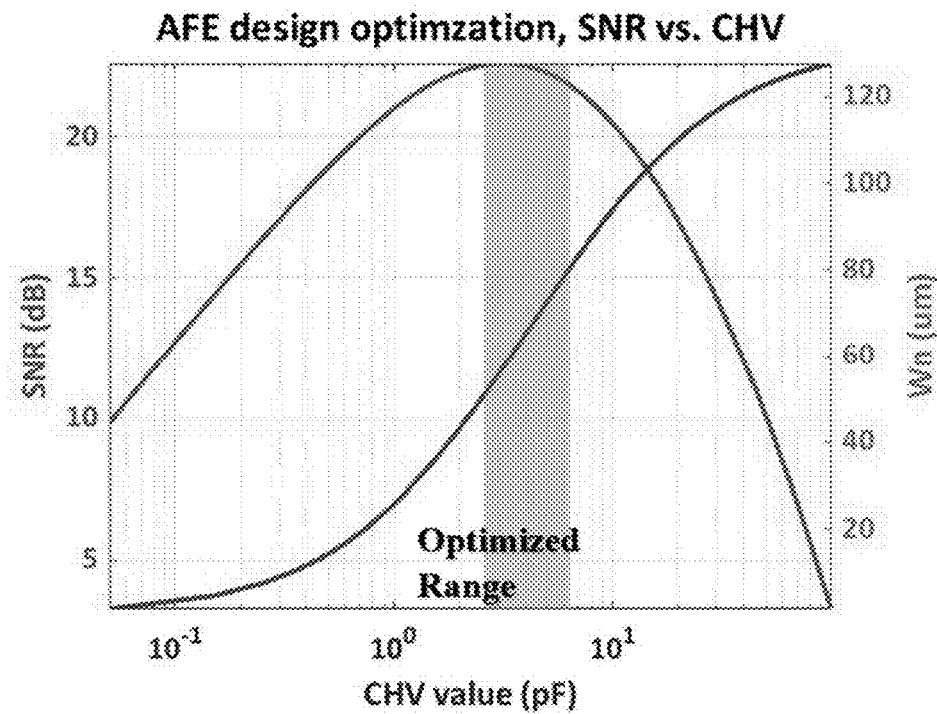
FIG. 13 is a plot showing total AFE signal-to-noise ratio (SNR) and LNA NMOS width vs. $C_{HV}$ value from the experiment described below.

With process dependent parameter $\kappa$ and $\gamma$, $C_{HV}$ was selected by optimizing the trade-off between input signal amplitude and amplifier gain (FIG. 13). With a constraint of minimum signal chain gain of 3 V/V, the SNR was maximized with $C_{HV}=2-5$ pF. The design used $C_{HV}=3.45$ pF to account for fabrication tolerance.

Results

Figure 14:
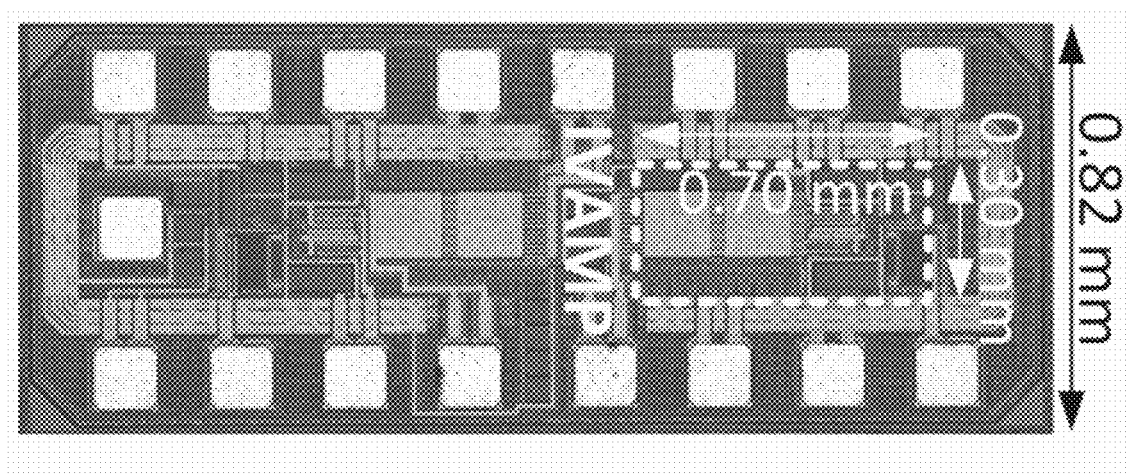
FIG. 14 is a die photograph of the fabricated AFE ASIC from the experiment described below.
Figure 15:
FIG. 15 is a photograph of the AFE-ASIC and PMUT-TrFE integrated on a miniaturized PCB that was mounted on the tip of a standard 1 mm catheter from the experiment described below.

The AFE ASIC was fabricated using the OnSemi I3T80 0.35-μm process (FIG. 14). Each chip had a fully integrated analog front end, an isolated high voltage capacitor, an isolated low noise amplifier and limiter, and an isolated buffer. This allowed the analog front end to be tested as a whole or in parts. The integrated circuits were wirebonded into SO-20 packages for bench test. The fabricated chip (including test circuits) was small enough to be integrated with the PMUT-TrFE transducer on a PCB within a standard 1 mm diameter catheter (FIG. 15).

High Voltage Capacitor Testing

Using an impedance analyzer (Agilent 4395A, Agilent Technology), the coupling capacitor ($C_{HV}$) for two chips were measured. The values of 3.46 pF and 3.66 pF were close to the designed value and well within the optimized range.

During imaging, the 100-V high voltage pulses could potentially stress the capacitors. To determine capacitor stability, an unpulsed coupling capacitor was subjected to 100-V pulses and the capacitor value was measured over 2M pulse cycles (Table I). Recorded data showed no degradation of the coupling capacitors under high voltage pulses.

TABLE I

| CHV MEASURED AFTER 100-V PULSING | | | | | |
|---|---|---|---|---|---|
| Cycles Pulsed | 10 k | 100 k | 500 k | 1 M | 2 M |
| $C_{HV}$ Measured (pF) | 3.46 | 3.40 | 3.46 | 3.44 | 3.46 |

Pulse Recovery

IVUS imaging requires the amplifier to recover quickly post-pulsing to receive the small signal echo from tissue. To image blood vessel walls only 0.5 mm away from the tip of the catheter, the amplifier must recover within 667 ns after pulsing, based on the speed of sound in blood.

Figure 16:
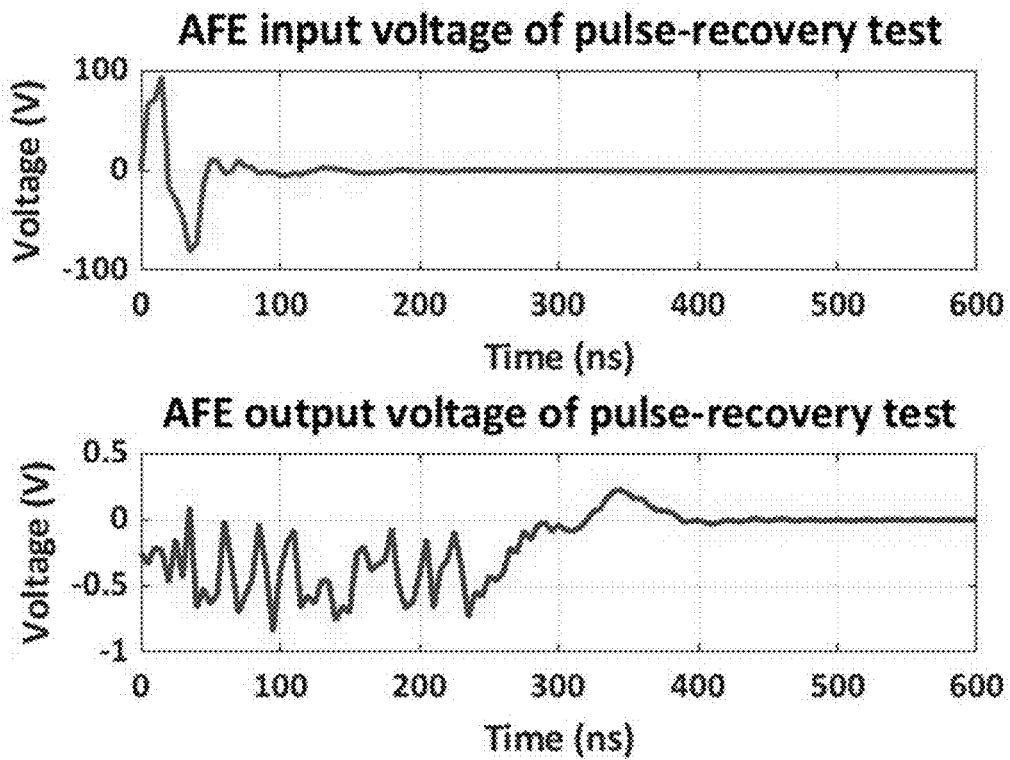
FIG. 16 is shows plots the AFE input (a) and output (b) voltage recovery during a pulsing cycle from the experiment described below.

The LNA recovery time was tested with a commercial pulser (Avtech AVB1-3-C, Avtech Electrosystems). A 100V high voltage, 40-MHz monocycle pulse was applied to the input of the AFE to test the clamping ability of the active limiter and the post-pulse-recovery time of the amplifier. As a result, the amplifier's output voltage was kept well below breakdown voltage, and the amplifier recovered ~500 ns after pulsing (FIG. 16). The measured recovery time was significantly less than 667 ns and suitable for IVUS imaging.

Signal Amplifier Testing

Figure 17:
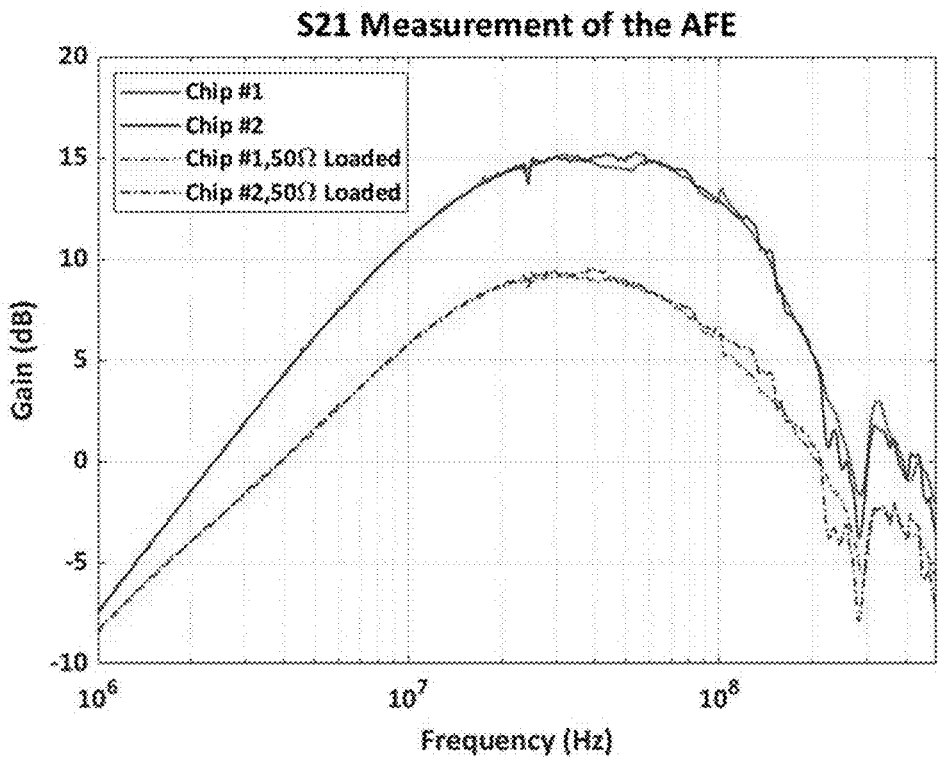
FIG. 17 is a plot of the gain of different chips over a wide frequency range from the experiment described below.

The AFE had an unloaded gain of 15 dB (Agilent 4395A, Agilent Technology) and a −3 dB bandwidth of 110 MHz. When loaded with 50Ω, the AFE had a −3 dB bandwidth of 92 MHz, and a unity-gain bandwidth of 225 MHz (FIG. 17).

To calculate the total signal chain gain, which includes the insertion loss (IL) between the PMUT-TrFE and AFE, IL was modeled and applied to the S21 measurement. Given that PMUT-TrFE was modeled as a capacitor with 2.2 pF capacitance with 30 kΩ leakage resistance at 40 MHz, and the coupling capacitor was 3.45 pF, IL≅5.2 dB at 40 MHz. As a result, the loaded total signal chain was 9.8 dB at 40 MHz.

The analog front end was tested to have an SNR of 20.1 dB at the output assuming a transducer-referred input signal amplitude of 1 mV. The noise performance was significantly better than this baseline.

The output impedance of the buffer at the end of the signal chain was well matched to 50Ω. The output impedance of the AFE was measured with an impedance analyzer (Agilent 4395A, Agilent Technology) to be 53.7Ω and 51.7Ω for the two chips tested.

Pulse-Echo Testing

Figure 18:
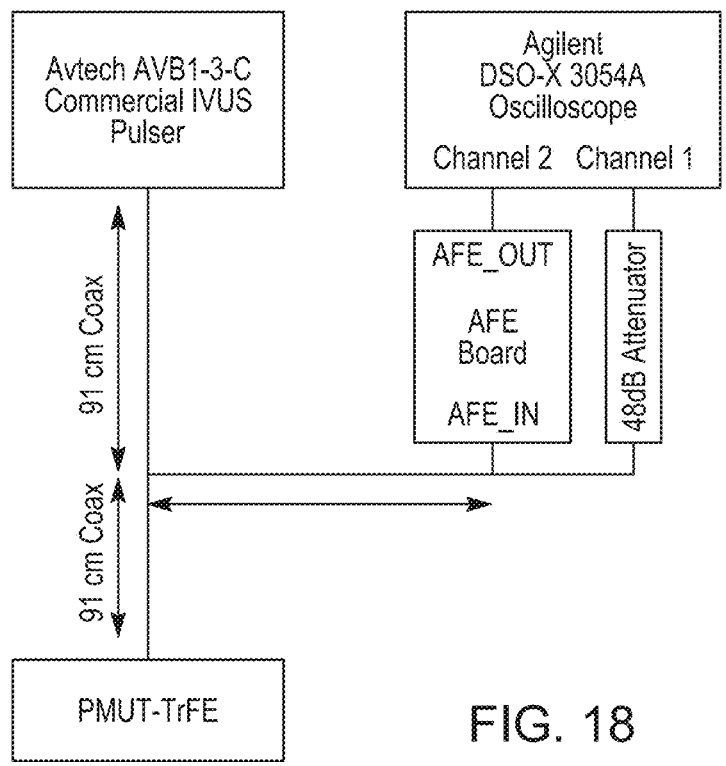
FIGS. 18 and 19 are examples of the test setup from the experiment described below.
Figure 19:
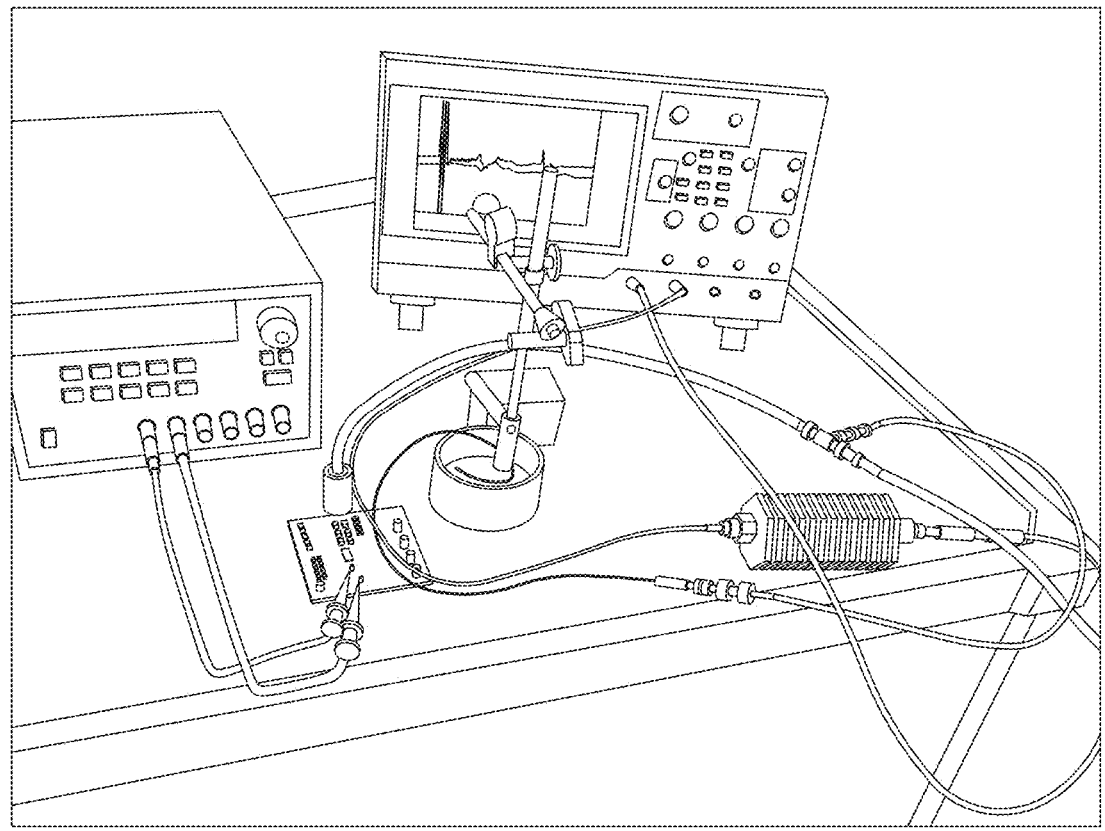

To demonstrate the AFE ASIC's ability to work with the PMUT-TrFE transducer in an integrated IVUS system, a test system was set up for a pulse-echo test (FIGS. 18 and 19). A test PMUT-TrFE was mounted on a small PCB and immersed in water in a beaker. The test PMUT-TrFE was positioned so that the bottom of beaker was one focal length away. The test PMUT-TrFE board was connected to the input of the AFE. A commercial IVUS pulser was connected to the input of the AFE and PMUT to provide a high voltage 40 MHz monocycle pulse. Measurements were taken with a fast oscilloscope at the input of AFE (attenuated by 48 dB to protect the oscilloscope from direct pulsing) and the output of AFE.

The test successfully demonstrated that the AFE ASIC interfaces well with the PMUT. The AFE ASIC duplexed high voltage pulses and echo signals and amplified and buffered the echo signal into a 50Ω system. This basic test demonstrated pulse-echo transmission and reception with a received signal amplitude of about 100 mV.

Alternate Shaping Technique

Figure 20:
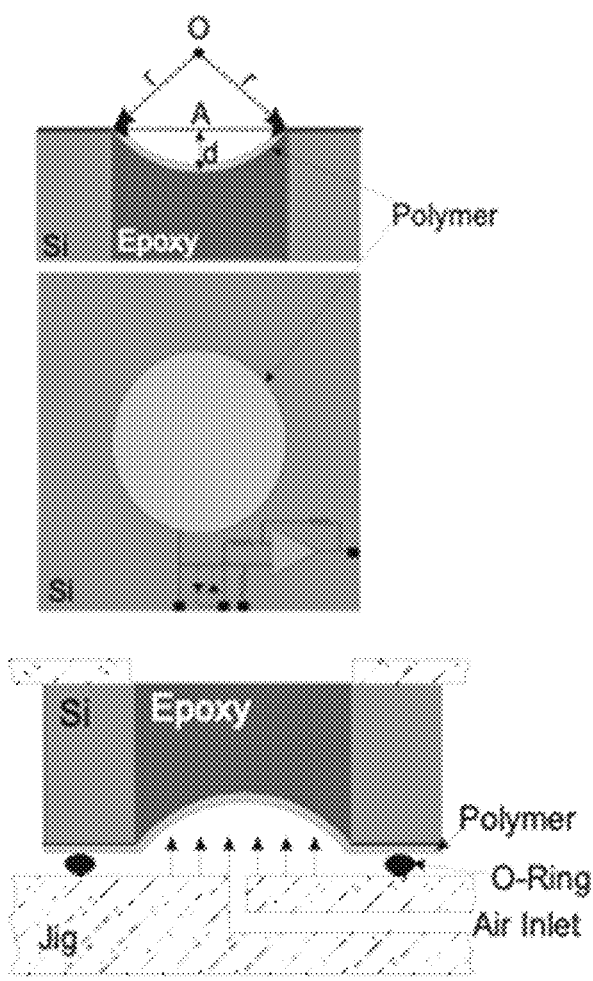
FIG. 20 is an example shaping technique that can be used to create a H-IVUS dielectric.
Figure 21:
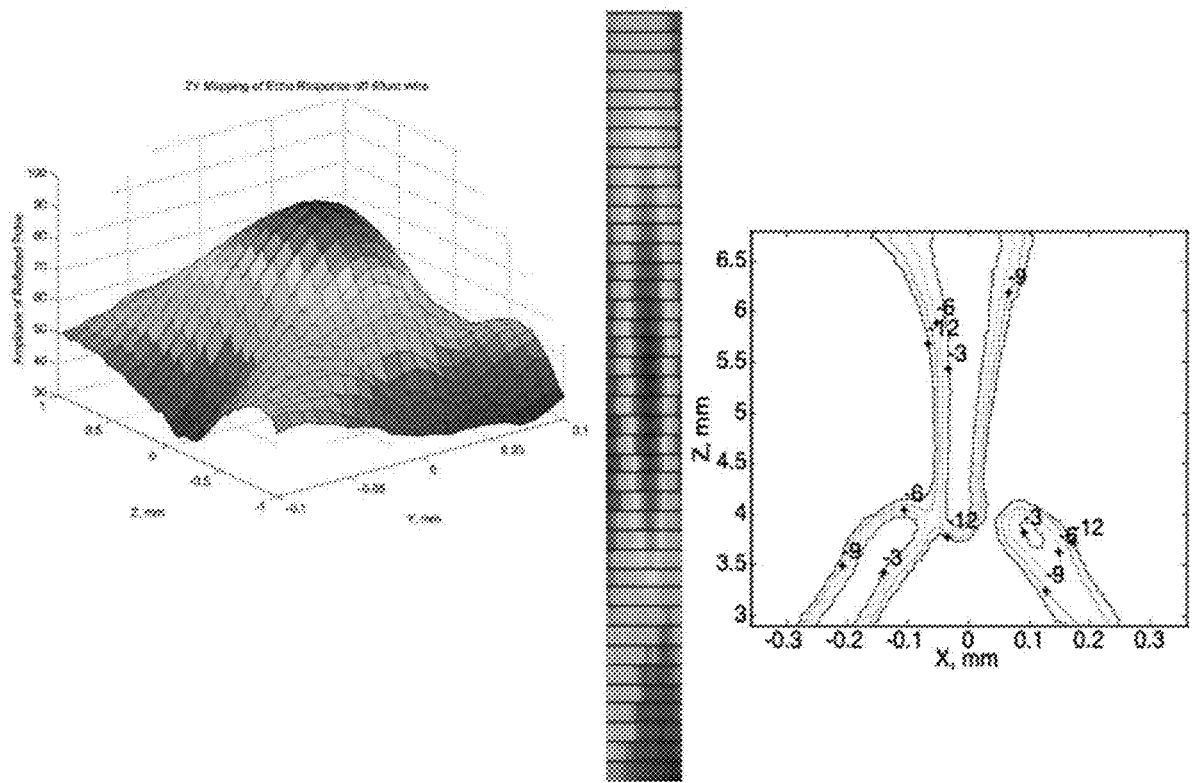
FIGS. 21 and 22 show theoretical radiation patterns produced by the H-IVUS dielectric of FIG. 20.
Figure 22:
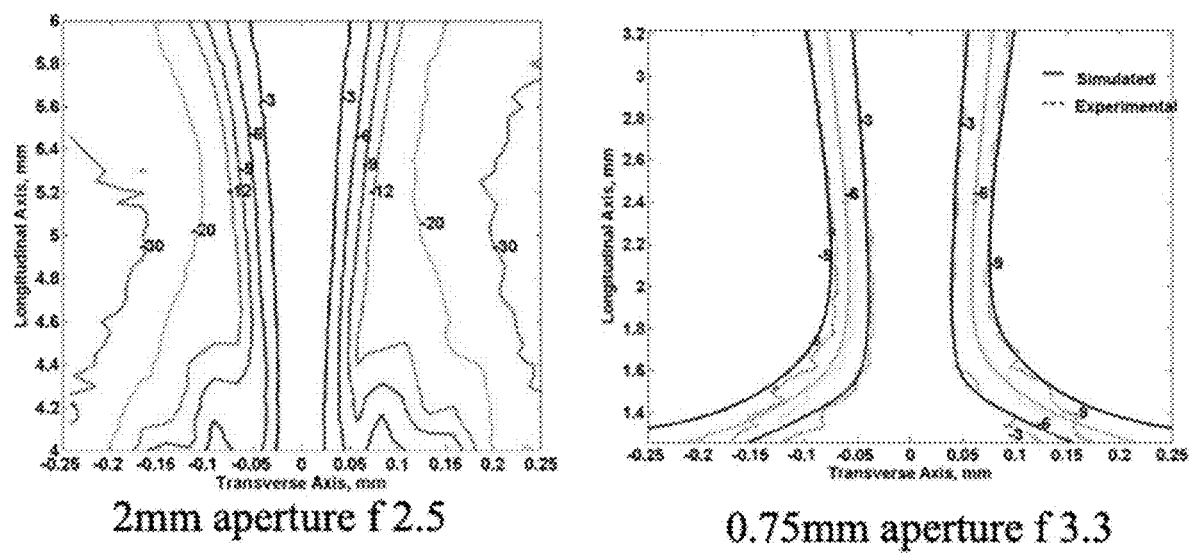

Air pressure can be used to create spherically shaped sections, with f=r/A, the aperture is fixed by the size of the hole, the f value can be controlled by controlling the diameter (2r), and diameter can be controlled by air pressure. Shown in FIG. 20 is an example shaping technique that can be used to create a H-IVUS dielectric. This shaping technique can be used to create a multiplicity of focus transistors (greater than 2) using air pressure of a form with circular perforations. Devices can be singulated and placed into holes in a printed circuit board with circuitry using a pick and place method (an example of the multiplicity is shown in FIG. 4). FIGS. 21 and 22 show theoretical radiation patterns produced by the H-IVUS dielectric of FIG. 20; The theoretical radiation patterns have a long focal region with a narrow beam width.

Harmonic Imaging

Figure 23:
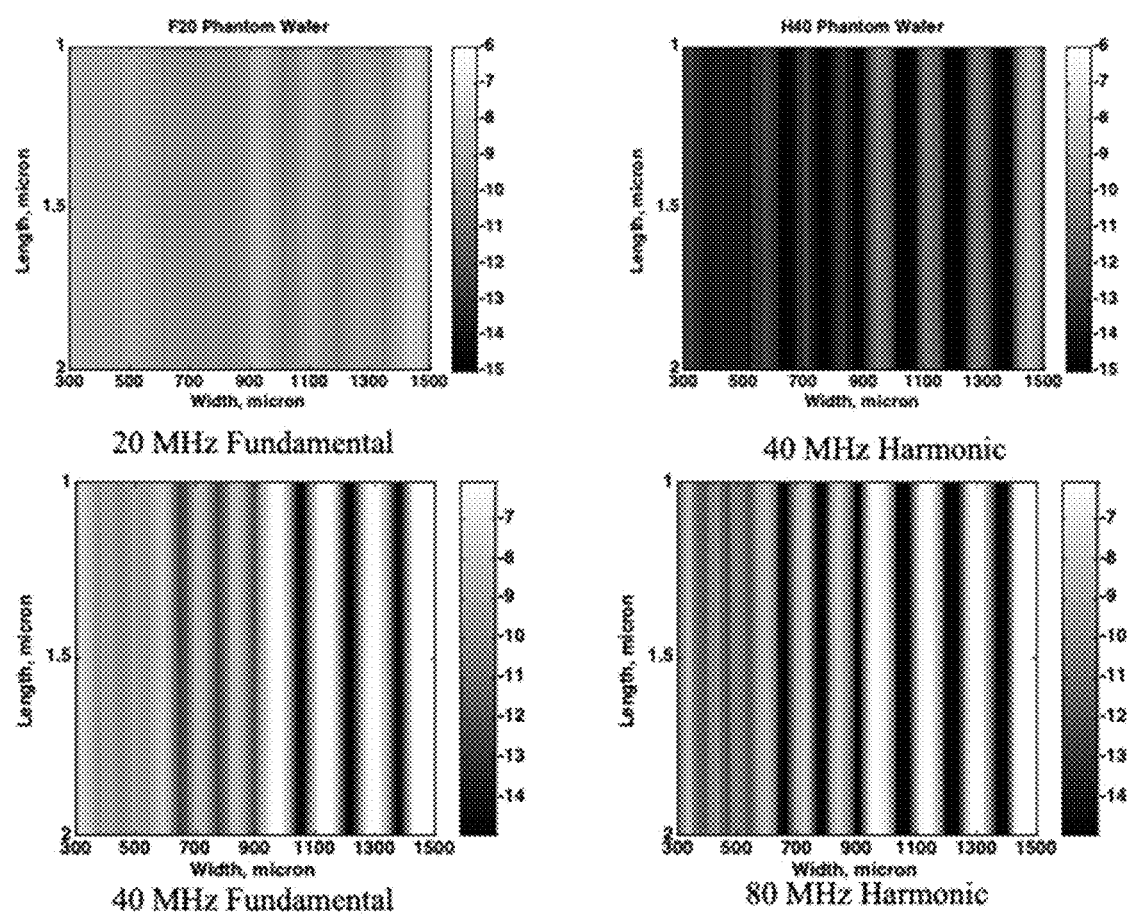
FIG. 23 shows fundamental and harmonic images from a MEMS phantom.

Tissue is an acoustically non-linear material. Sound propagating though tissue will produce harmonic overtones of the fundamental transmit frequency. Such harmonic overtones can be used to produce images with higher contrast and resolution. Additionally, these harmonic overtones can possibly yield additional information about tissue based on non-linear tissue properties. However, any imaging exploiting the harmonic overtones requires a broad band high frequency ultrasonic transistor. FIG. 23 shows fundamental and harmonic images from a MEMS phantom with fixed lines and spaces micromachined into a silicon wafer.

Figure 24:
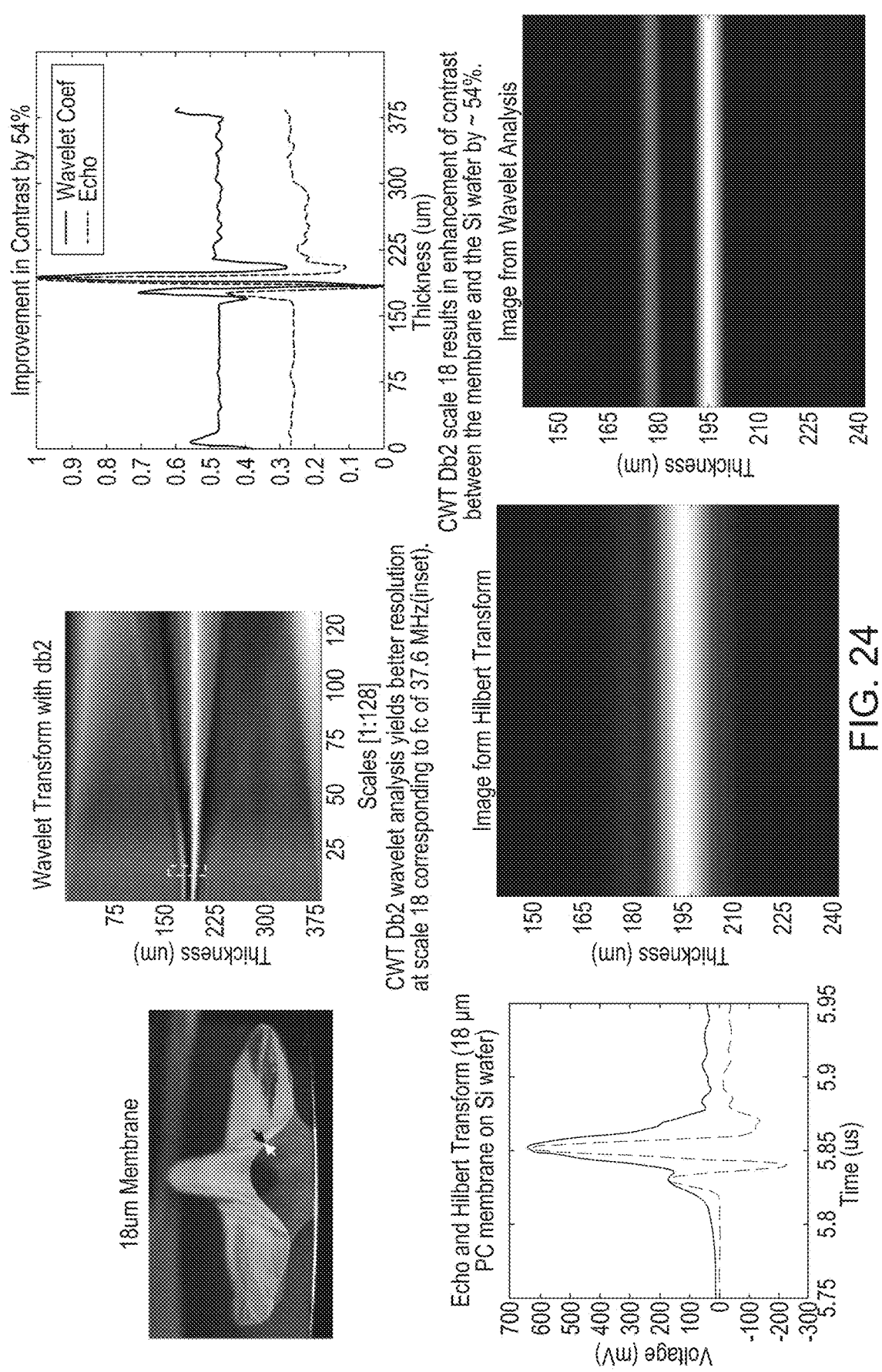
FIG. 24 is an example of resolving thin membranes with magnetic resonance angiography (MRA).

This can be very useful when imaging thin membranes, such as those of blood vessels and/or stents. FIG. 24 is an example of resolving thin membranes with magnetic resonance angiography (MRA).

From the above description, those skilled in the art will perceive improvements, changes, and modifications. Such improvements, changes and modifications are within the skill of one in the art and are intended to be covered by the appended claims.

What is claimed is:

1. A high-resolution intravascular ultrasound (H-IVUS) transducer assembly comprising:
   a printed circuit having one or more electrical signal conditioners, each of the one or more electrical signal conditioners comprising one or more front-end interface amplifiers and dual high voltage coupling capacitors in series; and
   one or more convertors made of a polymer and configured to convert electrical energy to acoustic energy and acoustic energy to electrical energy,
   wherein the one or more convertors are interfaced to a pre-shaped receiving area of the printed circuit with at least a conductive material and shaped into a generally concave shape after being placed on the printed circuit,
   wherein the pre-shaped receiving area comprises a material that is permanently deformable under pressure and/or heat, wherein the material has at least one acoustic property that is complementary to at least one acoustic property of the polymer of the one or more convertors to convert electrical energy to acoustic energy and acoustic energy to electrical energy.

2. The H-IVUS transducer assembly of claim 1, wherein the polymer comprises a piezoelectric polymer that is thermoplastic.

3. The H-IVUS transducer assembly of claim 2, wherein the thermoplastic comprises polyvinylidene difluoride (PVDF) and/or polyvinylidene difluoride trifluoroethylene (PVDF-TrFE).

4. The H-IVUS transducer assembly of claim 1, wherein the one or more electrical signal conditioners are embodied on one or more application specific integrated circuits (ASICs).

5. The H-IVUS transducer assembly of claim 1, wherein at least one of the one or more electrical signal conditioners is configured to interface with the one or more convertors.

6. The H-IVUS transducer assembly of claim 1, wherein at least a portion of the conductive material comprises a curable conductive fluid, and/or
   wherein the one or more convertors are interfaced to the printed circuit with a non-conductive epoxy.

* * * * *